(12) United States Patent
Bhumiratana et al.

(10) Patent No.: US 11,517,647 B2
(45) Date of Patent: Dec. 6, 2022

(54) POROUS POLYMER SCAFFOLD AND PREPARATION METHOD THEREOF

(71) Applicant: EpiBone, Inc., Brooklyn, NY (US)

(72) Inventors: Sarindr Bhumiratana, Oceanside, NY (US); Eric Jeffries, Warrington, PA (US); Melanie Horwitz, New York, NY (US)

(73) Assignee: EPIBONE, INC., Brooklyn, NY (US)

( * ) Notice: Subject to any disclaimer, the term of this patent is extended or adjusted under 35 U.S.C. 154(b) by 0 days.

(21) Appl. No.: 16/080,880

(22) PCT Filed: Feb. 28, 2017

(86) PCT No.: PCT/US2017/019956
§ 371 (c)(1),
(2) Date: Aug. 29, 2018

(87) PCT Pub. No.: WO2017/151619
PCT Pub. Date: Sep. 8, 2017

(65) Prior Publication Data
US 2019/0083681 A1 Mar. 21, 2019

Related U.S. Application Data

(60) Provisional application No. 62/301,280, filed on Feb. 29, 2016.

(51) Int. Cl.
| | |
|---|---|
| *A61L 27/46* | (2006.01) |
| *A61L 27/18* | (2006.01) |
| *A61L 27/50* | (2006.01) |
| *A61L 27/44* | (2006.01) |
| *A61L 27/54* | (2006.01) |
| *A61L 27/56* | (2006.01) |
| *C08L 67/04* | (2006.01) |

(52) U.S. Cl.
CPC ............... *A61L 27/46* (2013.01); *A61L 27/18* (2013.01); *A61L 27/446* (2013.01); *A61L 27/50* (2013.01); *A61L 27/54* (2013.01); *A61L 27/56* (2013.01); *A61L 2300/406* (2013.01); *A61L 2300/604* (2013.01); *A61L 2300/64* (2013.01); *A61L 2430/02* (2013.01); *C08L 67/04* (2013.01)

(58) Field of Classification Search
None
See application file for complete search history.

(56) References Cited

U.S. PATENT DOCUMENTS

| | | |
|---|---|---|
| 8,328,876 B2 | 12/2012 | Behnam et al. |
| 8,722,075 B2 | 5/2014 | Shimp et al. |
| 8,865,199 B2 | 10/2014 | Coleman et al. |
| 8,906,362 B2 | 12/2014 | Ferguson et al. |
| 9,163,212 B2 | 10/2015 | McKay |
| 9,597,359 B2 | 3/2017 | Mao et al. |
| 9,775,931 B2 | 10/2017 | Francis et al. |
| 9,938,502 B2 | 4/2018 | Zhang et al. |
| 9,987,394 B2 | 6/2018 | Meretzki |
| 10,479,977 B2 | 11/2019 | Wang et al. |
| 10,736,991 B2 | 8/2020 | Badylak et al. |
| 10,864,234 B2 | 12/2020 | Tuan |
| 2009/0292360 A1 | 11/2009 | Borden |
| 2011/0313538 A1 | 12/2011 | Oh et al. |
| 2014/0371869 A1* | 12/2014 | Atala ............... A61K 38/18 623/23.61 |
| 2015/0024063 A1 | 1/2015 | Lu et al. |

FOREIGN PATENT DOCUMENTS

WO 2011/123110 A1 10/2011

OTHER PUBLICATIONS

Khojasteh et al (J Biomed Mater Res Part B 848-854, 2013) (Year: 2013).*
Mi et al (J Cellular Plastics 51:165-196, first published Apr. 14, 2014) (Year: 2014).*
Vogt et al (Euro Cell and Mater 4:30-38, 2002) (Year: 2002).*
Sharaf et al (J Oral Maxillofac Surg 70:647-656, 2012) (Year: 2012).*
Zhang et al (J Appl Polym Sci 130:3509-3520, 2013) (Year: 2013).*
Lu et al (J Mater Sci: Mater Med, 10 pages, 2012) (Year: 2012).*
Guarino et al., "Porosity and mechanical properties relationship in PCT porous scaffolds," Journal of Applied Biomaterials & Biomechanics, 2007, vol. 5, No. 3, pp. 149-157.
Li et al., "Fabrication and Characterization of Bioactive Wollastonite/PHBV Composite Scaffolds," Biomaterials, vol. 25, 2004, pp. 5473-5480.
International Search Report and Written Opinion Issued in International Application No. PCT/US2017/019956 dated May 19, 2017.
European Search Report issued in European Application No. 17760613.4 dated Aug. 16, 2019.
Minton, J. et al., "Design and fabrication of polymer/ceramic scaffolds for bone tissue engineering", 71st Annual Technical Conference for the Society of Plastics Engineers 2013, ANTEC 2013 Apr. 22, 2013-Apr. 24, 2013, Society of Plastics Engineers, vol. 2, Jan. 1, 2013, pp. 1145-1150.
Minton, J. et al., "Solvent-free polymer/bioceramic scaffolds for bone tissue engineering: fabrication, analysis, and cell growth", Journal of Biomaterials Science, Polymer Edition, vol. 25, No. 16, Nov. 2, 2014, pp. 1856-1874.

(Continued)

*Primary Examiner* — Craig D Ricci
(74) *Attorney, Agent, or Firm* — Troutman Pepper Hamilton Sanders LLP (57) ABSTRACT

The present invention relates to a porous polymer material (or scaffold), and more particularly to a polymer-ceramic composite having interconnected pores and a porosity of about 50% to 90%. The scaffold is bioresorbable and exhibits advantageous mechanical properties that mimic those found in natural bone. Methods of preparing the scaffolds and using them in skeletal tissue engineering applications (e.g., as bone grafts to repair osteochondral defects and ligaments) is also described.

19 Claims, 10 Drawing Sheets

(56) References Cited

OTHER PUBLICATIONS

Yong, L. et al, "Preparation and Mechanical Properties of Porous [beta]-tricalclum phosphate/poly(L-lactic acid) Composite Scaffold Materials", Rare Metal Materials and Engineering Northwest Inst. Nonferrous Met. Res. China, vol. 34, No. 6, Jun. 2005, pp. 1208-1211, with English Abstract.

* cited by examiner

POROUS POLYMER SCAFFOLD AND PREPARATION METHOD THEREOF

CROSS-REFERENCE TO RELATED APPLICATIONS

This application is a National Stage of International Application No. PCT/US2017/019956, filed Feb. 28, 2017, which claims the benefit of U.S. Provisional Application No. 62/301,280, filed Feb. 29, 2016, the contents of each of which are herein fully incorporated by reference in their entirety.

FIELD OF THE INVENTION

The present invention relates to a porous polymer material (or scaffold), and more particularly to a polymer-ceramic composite having interconnected pores and a porosity of about 50% to 90%. The scaffold is bioresorbable and exhibits advantageous mechanical properties that mimic those found in natural bone. Methods of preparing the scaffolds and using them in skeletal tissue engineering applications (e.g., as bone grafts to repair bone, osteochondral, and ligament defects) is also described.

BACKGROUND

Artificial polymer-based bone graft material made to closely resemble natural bone would be a useful replacement for natural bone in various clinical applications (e.g., bone repair and reconstruction). Acceptable synthetic bone can avoid problems of supply availability and the risks and complications associated with allograft bone, such as risks of infection, disease, and viral transmission.

Accordingly, there is a great need in the art for effective scaffolds that are bioresorbable and resemble natural bone. This invention addresses these and other needs.

SUMMARY OF THE INVENTION

In some embodiments, the present invention relates to a porous polymer scaffold comprising a polymer (e.g., polycaprolactone) and an inorganic additive (e.g., tricalcium phosphate), the scaffold having interconnected pores and a porosity range of about 50% to about 90%. In some embodiments, the porous scaffold has a pore size ranging from about 500-800 µM.

In some embodiments, the porous scaffold is a bioresorbable scaffold, optionally comprising a bioreactive agent (e.g., mesenchymal stem cells). In other embodiments, the scaffold provides a suitable platform for stem cell differentiation.

The present invention also provides, in some embodiments, a method of preparing the porous scaffold, comprising the steps of:
  heating a mixture comprising a biodegradable polymer, an inorganic additive (or ceramic material), and a porogen (e.g., NaCl);
  compressing the heated mixture at a pressure of about 10 MPa to about 110 MPa;
  cooling the compression to form a bulk substrate;
  selectively removing a material from the bulk substrate to afford a shaped substrate; and
  removing the porogen from the shaped substrate to afford the porous scaffold having a desired shape.

In some embodiments, the invention further provides a bone graft composition comprising the porous scaffold.

The present invention also provides a method of treating a bone defect site in a patient, for example, by applying to the defect site a bone graft composition comprising the porous scaffold of the invention. The bone graft may be implanted surgically to the site and may contain differentiated stem cells (e.g., mesenchymal stem cells and/or adipose derived stem cells, hADSC) harvested from the patient or another donor.

DETAILED DESCRIPTION

The present invention provides an artificial polymer-based bone scaffold that, when implanted in the body, acts as a template that that allows the body's own cells to grow and form new tissues while the scaffold is gradually absorbed. The scaffold is a highly porous and biocompatible material, comprising a polymer (e.g., polycaprolactone) and an inorganic additive (e.g., tricalcium phosphate) and has interconnected pores throughout the structure. Applicants have surprisingly discovered that the scaffold has numerous advantageous properties, including but not limited to: a) being highly porous with an interconnected pore network that facilitates cell growth and nutrient delivery throughout the structure; b) promoting cell attachment and differentiation; c) having mechanical properties that mimic those of natural bone and that permit machining the scaffold into a suitable shape; and d) being biocompatible and bioresorbable.

The scaffold is not limited to any particular form and may be in the form of any rigid object or in the form of an anatomical shape. In some embodiments the scaffold is a de-cellularized object or material. In some embodiments, the scaffold is cellularized. In some embodiments, the term "scaffold" includes, but is not limited to, a biological or artificial tissue engineering carrier matrix for tissue-regenerating cells. A scaffold may be a biocompatible scaffold, a bioactive scaffold or a degradable scaffold.

Polymers:

The scaffold of the invention contains a polymer material, for example a bioresorbable polymer. In general, the term "bioresorbable polymer" (or degradable polymer) includes any polymer material that can be safely absorbed in the body such that the material from which a scaffold is made disappears over time. Bioresorbable polymers (both natural and synthetic) are well known in the art and include, but are not limited to, polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), polyvinylpyrrolidone, polyethylene glycol, polyhydroxycellulose, chitin, chitosan, poly(L-lactic acid), poly(lactide-co-glycolide), poly(hydroxybutyrate-co-valerate), and copolymers, terpolymers, or combinations or mixtures of the above materials. In some embodiments, the bioresorbable polymer comprises silk, poly(ethylene glycol) diacrylate (PEGDA), or poly(ethylene glycol) (PEG). Suitable bioresorbable polymers can be chosen by the person skilled in the art using standard techniques and based on the mechanical and degradation properties of the polymer such that the polymer is chosen for its compatibility with, for example, bone remodeling.

In some embodiments, the bioresorbable polymer or polymer composite comprises polycaprolactone (PCL, e.g., at 40-80 kDa) or a PCL-ceramic composite mesh.

In some embodiments, the bioresorbable polymer or polymer composite comprises poly(lactic-co-glycolic acid) (PLGA).

In some embodiments, the bioresorbable polymer or polymer composite comprises poly(lactic acid) (PLLA).

In some embodiments, the bioresorbable polymer or polymer composite comprises polyhydroxybutyrate (PHB).

In some embodiments, the bioresorbable polymer or polymer composite comprises poly(lactide-co-caprolactone) (PLCL).

In some embodiments, the bioresorbable polymer comprises poly(3-hydroxybutyrate-co-3-hydroxyvalerate) (PHBV) or a PHB-PHV copolymer.

Additives:

The mechanical properties and degradation time of the scaffold can be tailored by adjusting, for example, the molecular weight, hydrophilicity, and/or crystallinity of the bioresorbable polymer. This can be achieved, for example, by varying the percentage of polymer (e.g., polycaprolactone) with respect to certain additives. In some embodiments, the bioresorbable polymer is combined with a ceramic material to produce a polymer-ceramic composite. Suitable ceramics include, for example, inorganic additives such as tricalcium phosphate (TCP) or hydroxyapatite (HA). Tricalcium phosphate is a calcium salt of phosphoric acid with the chemical formula $Ca_3(PO_4)_2$. Calcium phosphate is one of the main combustion products of bone. Hydroxyapatite is a naturally occurring mineral form of calcium apatite with the formula $Ca_5(PO4)_3(OH)$. Up to 50% by volume and 70% by weight of human bone is a modified form of hydroxyapatite. Other ceramics include, for example, biphasic calcium phosphate (BCP) and bioglass. Other suitable additives include, but are not limited to, bone powder, and/or calcium phosphate.

Pore Size/Porosity:

The scaffold is sufficiently porous to allow, for example, seeding and growth of cells. For example, the size of the pores can be adjusted to optimize cell survival and proliferation. In some embodiments, the pores are at least about 50 µm to at least about 850 µm in diameter.

In some embodiments, the pore size is about 60 µm, 70 µm, 80 µm, 90 µm, 100 µm, 120 µm, 140 µm, 160 µm, 180 µm, 200 µm, 220 µm, 240 µm, 260 µm, 280 µm, 300 µm 320 µm, 340 µm, 360 µm, 380 µm, 400 µm, 420 µm, 440 µm, 460 µm, 480 µm, 500 µm, 520 µm, 540 µm, 560 µm, 580 µm, 600 µm, 620 µm, 640 µm, 660 µm, 680 µm, 700 µm, 750 µm, 800 µm, or about 850 µm.

In some embodiments, the average pore size is from about 500 µm to about 800 µm.

In some embodiments, the average pore size from about 450 µm to about 600 µm.

The porosity (or void fraction or "empty space") of the scaffold can also be varied to allow seeding and cell growth. For example, in some embodiments, the porosity of the scaffold is at least about 30% to at least about 90%.

In some embodiments, the porosity is about, 30%, 35%, 40%, 45%, 50%, 55%, 60%, 65%, 70%, 75%, 80%, 85%, or about 90%.

In some embodiments, the porosity is about 40% to about 50% or about 50% to about 60% or about 50% to about 70%, or about 70% to about 80% or about 80% to about 90%.

In some embodiments, the porosity is from about 60% to about 80%.

In some embodiments, the porosity is about 50%.

In some embodiments, the porosity is about 50% to about 90%. In some embodiments, the pores are sufficiently interconnected so that cells can migrate throughout the scaffold. The interconnected pores can promote uniform cell seeding and nutrient delivery throughout the scaffold.

In some embodiments, the scaffold material is substantially uniform throughout the structure. For example, in some embodiments, the scaffold may be characterized as having very narrow pore size distributions (or variation) throughout the structure. In some embodiments, the average pore size at the surface of the scaffold is substantially similar to the average size of pores at other portions of the structure. In some embodiments the average pore size is uniform throughout the scaffold structure. In some embodiments, the average pore size distribution is less than about 200 µm, 190 µm, 180 µm, 170 µm, 160 µm, 150 µm, 140 µm, 130 µm, 120 µm, 110 µm, 100 µm, 75 µm, 50 µm, 40 µm, 30 µm, 20 µm, 10 µm, 9 µm, 8 µm, 7 µm, 6 µm, 5 µm, 4 µm, 3 µm, 2 µm, or about 1 µm.

In some embodiments, the average pore size distribution is less than about 10 µm.

In some embodiments, the average pore size distribution throughout the scaffold is less than about 5 µm. In some embodiments, the variation in average pore size throughout the structure is less than about 20%, 15%, 10%, 5%, 4%, 3%, 2%, or about 1%.

In some embodiments, the porosity (or void fraction or "empty space") of the scaffold is substantially uniform throughout the structure. For example, in some embodiments, the variation in porosity is less than about 20%, 15%, 10%, 5%, 4%, 3%, 2%, or about 1%. In some embodiments, the porosity at the surface of the scaffold is substantially similar to the porosity at other portions of the structure. In some embodiments the porosity is uniform throughout the scaffold structure.

In some embodiments, there exists a gradient of porosity or pore size. For example, in some embodiments, there are at least one or a plurality of separate regions within the scaffold that have distinct pore size or void fraction values. For instance, some work has demonstrated benefits of highly porous cartilage region (90%) and less porous bone region (75%).

In some embodiments, the scaffolds contain a highly porous region, having e.g., 80, 85, 90, or 95% porosity.

In some embodiments, the scaffolds contain a separate region having 60%, 65%, 70% or 75% porosity.

Scaffold Preparation:

In some embodiments, the scaffold material is manufactured by melt compressing polymer and/or polymer/ceramic (e.g., calcium phosphate powders) with porogens (or salt crystals such as NaCl), processing (or machining) the resulting bulk compression to a particular shape, and then leaching the embedded salt crystals to form a porous polymer/calcium phosphate adduct. In some embodiments, for example, a porous scaffold of polycaprolactone and tricalcium phosphate can be prepared. In this embodiment, polycaprolactone/tricalcium phosphate powders can be heated in the presence of salt crystals. The heated mixture is compressed (for example using a 39 MPa compression force), forcing a liquid polycaprolactone/tricalcium phosphate solution between the salt crystals. The compression is then cooled and resulting compression is machined to a desired shape, and the salt crystals are leached with a solvent (such as water), to afford the porous scaffold comprising polycaprolactone and tricalcium phosphate. The final material is biocompatible and osteo-conductive.

The salt crystals can comprise any salt (e.g., sodium chloride), or other porogen material, suitable for generating a porous construct for tissue engineering. Suitable porogens include, for example, sodium chloride or poly (methyl methacrylate) (PMMA). In some embodiments, the porogen is glucose or poly(vinyl alcohol).

The salt crystal particle size is chosen by a person skilled in the art using standard techniques to provide a desired pore size and interconnectivity to the resulting scaffold. In some embodiments, the particle size is at least about 50 μm to at least about 850 μm in diameter. In some embodiments, the particle size of the salt crystal porogen is about 60 μm, 70 μm, 80 μm, 90 μm, 100 μm, 120 μm, 140 μm, 160 μm, 180 μm, 200 μm, 220 μm, 240 μm, 260 μm, 280 μm, 300 μm 320 μm, 340 μm, 360 μm, 380 μm, 400 μm, 420 μm, 440 μm, 460 μm, 480 μm, 500 μm, 520 μm, 540 μm, 560 μm, 580 μm, 600 μm, 620 μm, 640 μm, 660 μm, 680 μm, 700 μm, 720 μm, 740 μm, 760 μm, 780 μm, 800 μm, 820 μm, 840 μm, 860 μm, 880 μm, 900 μm, 920 μm, 940 μm, 960 μm, 980 μm or about 1 mm. In some embodiments, the salt crystal has a particle size of about 500 μm.

In some embodiments, the polymer mixture is heated before the compression step. For example, the polymer mixture may be heated to a temperature of about 50° C., or about 55° C., 60° C., 65° C., 70° C., 75° C., 80° C., 95° C., 90° C., 95° C., 100° C., 110° C., 120° C., 130° C., 140° C., 150° C., 160° C., 170° C., 180° C., 190° C., 200° C., 210° C., 220° C., 230° C., 240° C., 250° C., 260° C., 270° C., 280° C. or about 300° C. In some embodiments, the polymer mixture is heated to 220° C., e.g., for mixtures comprising PLLA.

In some embodiments, the polymer mixture is heated to a temperature of about 185° C. before the compression step.

Without being bound by any theory of the invention, it is believed that the high compression force used in the inventive process, which is applied before cooling, forces the salt crystals to come into contact with one another and displace gas, causing the pores to become advantageously interconnected throughout the scaffold. The polymer and tricalcium phosphate components are squeezed packed at a high pressure, then cooled until solidified. In some embodiments, pressures of about 5 MPa to about 25 MPa, or about 35 MPa to about 225 MPa, or about 35 MPa, 40 MPa, 45 MPa, 50 MPa, 55 MPa, 60 MPa, 65 MPa, 70 MPa, 75 MPa, 80 MPa, 85 MPa, 90 MPa, 95 MPa, 100 MPa, 150 MPa, 200 MPa or about 225 MPa are applied during the compression step. In one embodiment, a pressure of about 39 MPa is used.

The compressed bulk material may be processed or machined (e.g., lathed, subjected to computer numerical control ("CNC") automation, drilled or milled) before the salt leaching step, into any suitable shape. In general, a suitable shape is any shape compatible for the particular application of interest, for example as a bone graft. The shape of the scaffold may be a planar form or a three-dimensional form. Complicated three-dimensional shapes may also be prepared, for example in the form of a biological organ or tissue such as a body part or bone, or the like.

In some embodiments, the scaffold is shaped in the form of a biological tissue.

In some embodiments, the scaffold is shaped in the form a bone structure, for example a bone graft.

In some embodiments, the scaffold is shaped to conform to a bone structure being remodeled, e.g., an anatomical bone graft substitute (such as flat bones (cranium, maxilla, and rib), long bones (femur, tibia, ulna), and articulating surfaces (knee, hip, and temporomandibular joint), including a plate, pin, rod, screw, anchor, tack, arrow, stable, button, or any other regular or irregular shape, or a combination thereof.

Applicants have surprisingly discovered that the porosity and pore interconnectivity of the scaffolds can be preserved by carrying out the processing/machining step (or selectively removing material from the compressed bulk by way of milling, lathing, drilling, or cutting) prior to porogen leaching. This was unexpected in view of the known fragility of porous polymer materials, in which the surface porosity is usually abolished when subjected to high forces of machine processing. This is especially evident with soft polymers (e.g., PCL) which melt and ceramics/porogens (e.g., TPC and salt, respectively) which crumble during the machining step. However, Applicants have discovered that the conventional smearing of the surface layer (or undesired formation of a solid film layer on the surface) can be avoided using the above-described compression conditions, material composition, and method steps set forth herein. The scaffolds of the invention have an advantageous capacity to permit cells to infiltrate and remodel the construct during regeneration. In contrast, scaffolds with no or limited porosity are often encapsulated by a fibrous scar and fail to remodel properly.

Mechanical Properties:

The scaffold of the invention also exhibits certain advantageous mechanical properties which are useful, for example, in bone engineering applications. In some embodiments, for example, the mechanical properties of the scaffold match those found in natural bone. In one such embodiment, the scaffold has a Young's modulus (or elastic modulus) between about 0.1 and about 2 GPa or about 15 to about 20 GPa, or about 0.2 GPa, 0.4 GPa, 0.6 GPa, 0.8 GPa, 1.0 GPa, 1.2 GPa, 1.4 GPa, 1.6 GPa, 1.8 GPa, or about 2.0 GPa, or about 15 GPa, 16 GPa, 17 GPa, 18 GPa, 19 GPa, or about 20 GPa.

In some embodiments, the scaffold has a compressive strength of at least about 2.0 MPa to at least about 200 MPa, or more, or about 2.0 MPa, 5.0 MPa, 10 MPa, 15 MPa, 20 MPa, 25 MPa, 30 MP, 35 MPa, 40 MP, 45 MPa, 50 MPa, 55 MPa, 60 MPa, 65 MPa, 70 MPa, 75 MPa, 80 MPa, 85 MPa, 90 MPa, 95 MPa, 100 MPa, 150 MPa or about 200 MPa, or more.

In some embodiments, the scaffold has a compressive modulus value of at least about 50 MPa, 60 MPa, 70 MPa, 80 MPa, 90 MPa, 100 MPa, 120 MPa, 140 MPa, 160 MPa, 180 MPA, 200 MPa to at least about 500 MPa, or more, or about 250 MPa, 300 MPa, 350 MPa, 400 MPa, or about 450 MPa, or more.

In some specific embodiments, for example, the modulus is about 100 MPa for PHB-PHV scaffolds.

In some embodiments, the scaffold has a torsional strength of at least about 20 Nm, 30 nM, 40 Nm, to at least about 360 Nm, or more, or about 40 Nm, 60 Nm, 80 Nm, 100 Nm, 120 Nm, 140 Nm, 160 Nm, 180 Nm, 200 Nm, 240 Nm, 280 Nm, 320 Nm, 340 Nm, 360 Nm, 380 Nm, 400 Nm, 420 Nm, 440 Nm, 460 Nm, 480 Nm, or about 500 Nm or more.

In a some embodiments, the scaffold has a bending strength of at least about 50 Nm to at least about 600 Nm, or more. In some embodiments, the scaffold has a bending strength of at least about 50 Nm, 100 Nm, 150 Nm, 200 Nm, 250 Nm, 300 Nm, 350 Nm, 400 Nm, 450 Nm, 500 Nm, 550 Nm, or about 600 Nm, or more.

As is appreciated in the field of the invention, for example, as described in Guarino et. al., *Journal of Applied Biomaterials & Biomechanics,* 2007, 5(3) 149-157, which is hereby incorporated by reference in its entirety, the mechanical properties of the scaffold (e.g., stiffness and strength) can vary, based on certain properties, for example the density and pore geometry of the scaffold. Certain scaffolds, for example, those comprising poly-caprolactone polymer, can exhibit compressive modulus values ranging from about 0.1 MPa to about 2.0 MPa, or about 0.05 MPa, 0.06 MPa, 0.07 MPa, 0.08 MPa, 0.9 MPa, or about 0.2 MPa, 0.3 MPa, 0.4 MPa, 0.5 MPa, 0.6 MPa, 0.7 MPa, 0.8 MPa, 0.9 MPa, 1.0 MPa, 1.1 MPa, 1.2 MPa, 1.3 MPa, 1.4 MPa, 1.5 MPa, 1.6 MPa, 1.7 MPa, 1.8 MPa, or about 1.9 MPa. Suitable mechanical strength parameters are also disclosed in Li et al., *Biomaterials,* 25, 2004, 5473-5480 (PHBV polymer composites), which is hereby incorporated by reference in its entirety.

Method of Use:

The scaffolds of the invention are particularly useful for bone regeneration applications to replace or repair a bone defect, e.g., by surgical implantation of the scaffold. The scaffolds described here are also useful for long bone tissue engineering, for example, to augment the length of a bone in the upper and lower extremities of the human body. The scaffolds are also useful in bone engineering applications relevant to trauma (e.g., from an accident), congenital defects (e.g., people born without certain bones), and cancer such as ewings sarcoma. Other applications include using the scaffolds to mimic cartilage, ligament, & tendon interface with bone.

In some embodiment, the scaffold is implanted into a patient in need of bone regeneration or long bone tissue engineering.

The scaffold can be implanted with or without additional bioactive and/or inert agents or can be cultured in vitro with cells isolated from a donor, such as a patient, before implanting the scaffold into a patient. Pre-culturing of the scaffold promotes cellular proliferation and integration of the scaffold when implanted into the patient.

The scaffolds may be filled, packed, infused, adsorbed with, and/or absorbed with, suitable agents. Such agents can include, e.g., a bioactive agent, or an inert agent, and combinations thereof. Inert agents can be any suitable agent, e.g., carrier, excipient, sterilizing solution, labeling solution, and the like. Bioactive agents are also known in the art. For example, stem cells (e.g., mesenchymal stem cells), bone marrow, plasma, growth factors, proteins, antibiotics, and immunosuppressive agents, and combinations thereof. Scaffolds may also be surface treated (e.g., with plasma, or treatment with acid/base) to change chemical properties such as hydrophilicity. Additionally chemical conjugation (eg NHS-EDC conjugation) may be performed to attach bioactive functional groups to the surface.

The following examples are offered by way of illustration only and not by way of limitation.

EXAMPLES

Example 1. Polycaprolactone Scaffold

Polycaprolactone and tricalcium phosphate powders (2:1 ratio) were combined in the presence of sodium chloride salt crystals (average particle size of 850 μm). The mixture was heated to a temperature of 100° C. and then compressed at a force of 39 MPa using a hydraulic press. The compressed mixture was cooled to room temperature and sodium chloride salt crystals were leached from the solid by immersing the solid in a water solution with vigorous shaking. A porous polycaprolactone/tricalcium phosphate adduct was isolated, having an average porosity of 50-90% and an average pore size of about 600-800 μm.

Example 2. PHB-PHV2% Scaffold

Sodium chloride particles (450-600 μm) were mixed with PHB-PHV2% copolymer powder and compressed to 185° C. with 70 MPa pressure. The flat ends of the compress were lathed to remove film surface. Salt was removed by serial water washes.

Figure 1:
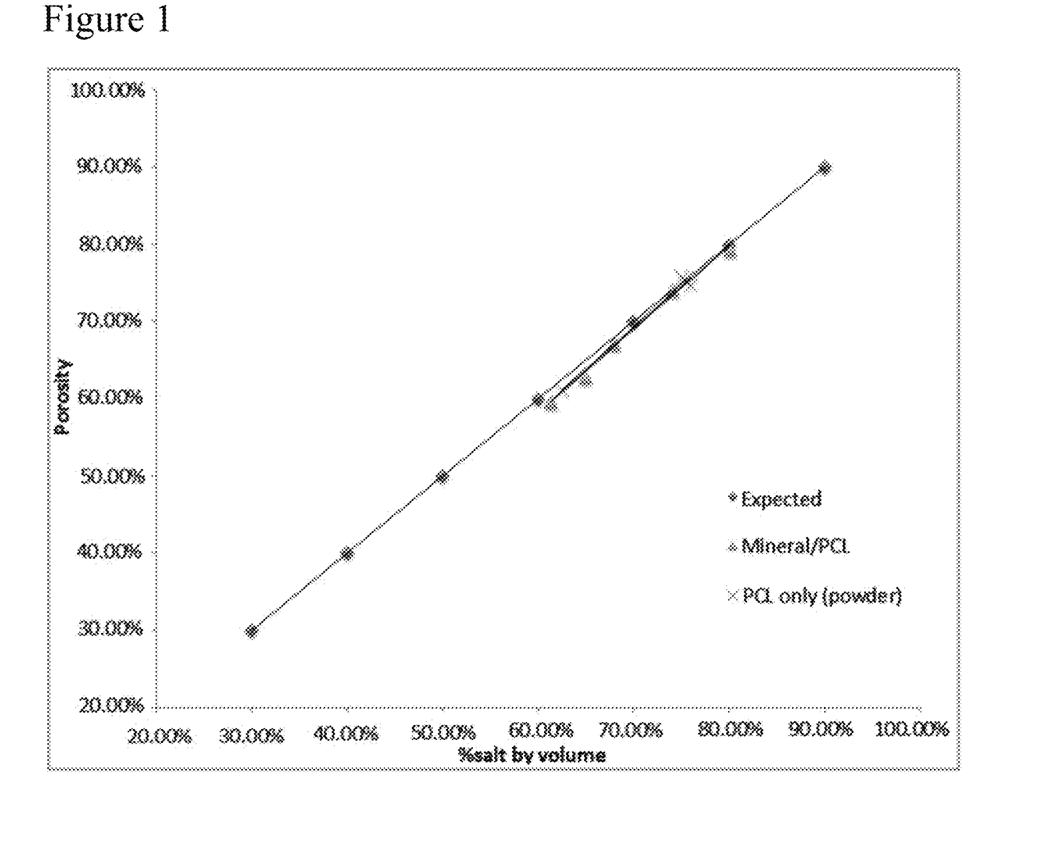
FIG. 1 is a graph showing porosity changes as a function of salt concentration for certain polymer scaffolds of the invention.
Figure 2:
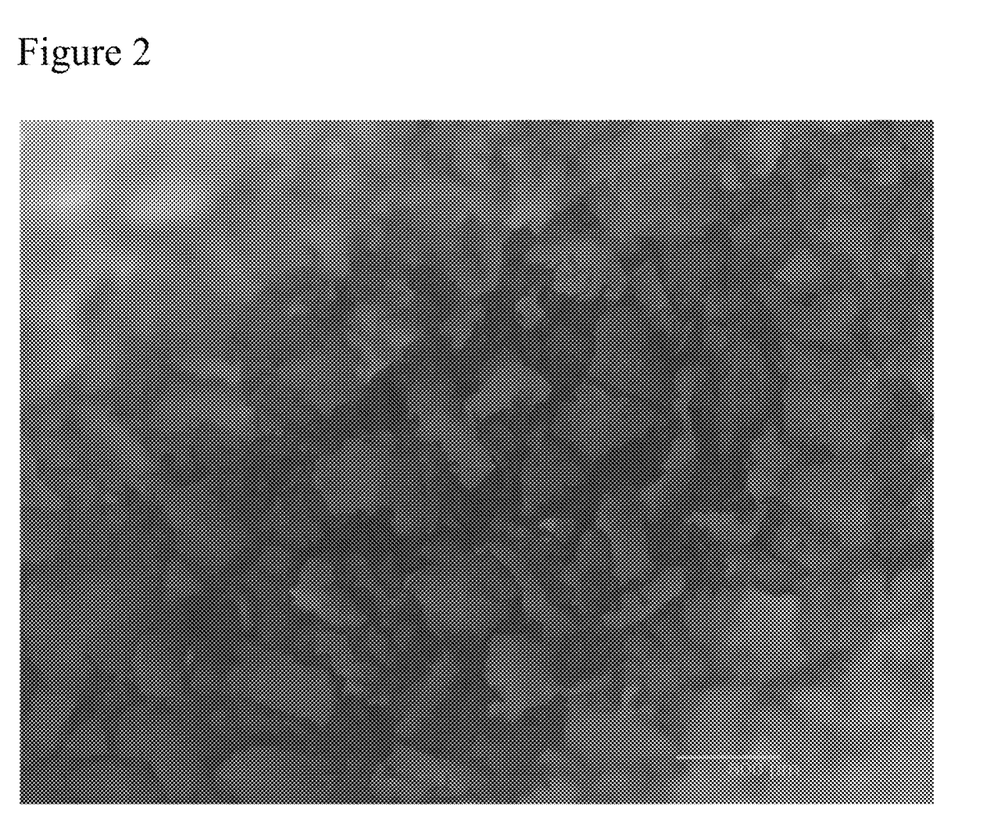
FIG. 2 is an illustration of a porous scaffold of the invention.
Figure 3:
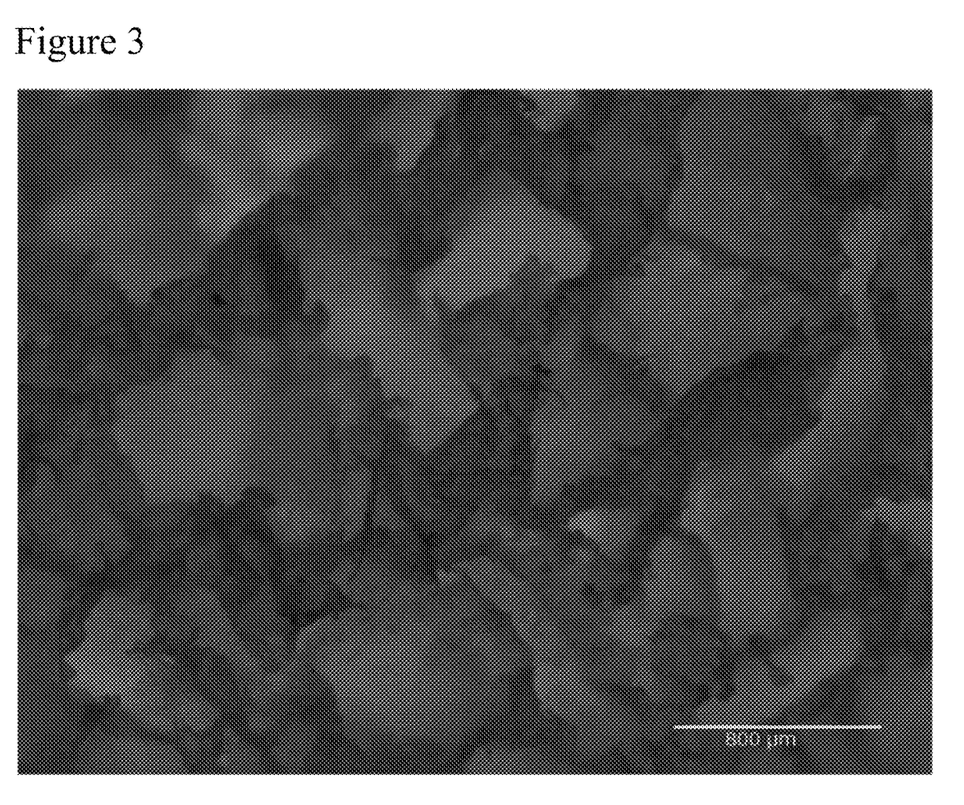
FIG. 3 is an illustration of a porous scaffold of the invention.
Figure 4:
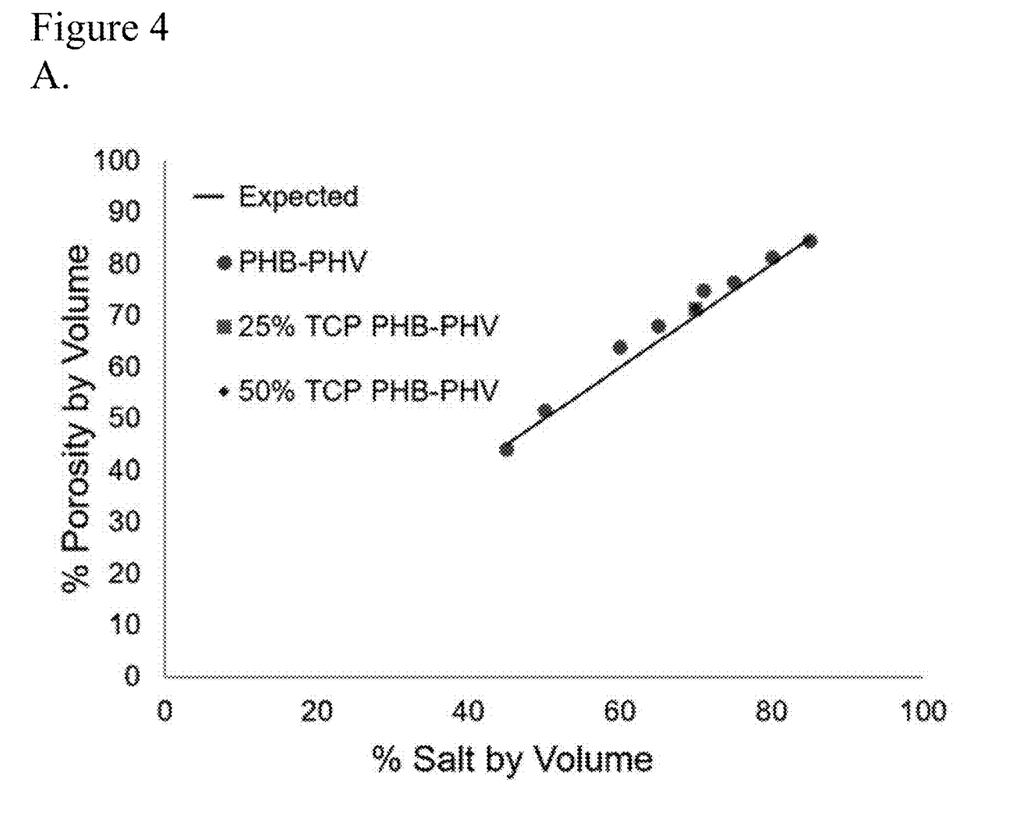
FIG. 4 is an graph showing: a) percent porosity by volume as a function of percent salt by volume for porous scaffolds of the invention, and b) MicroCT images of post-washed scaffolds of varying porosity.

Scaffolds with substitution of 25% tricalcium phosphate or 50% tricalcium phosphate were also prepared. Percent porosity by volume of the samples was determined, as shown in FIG. 4A, by converting mass change before and after the wash step via material density. Actual values closely follow predicted porosity based on starting mass. In FIG. 4B, μCT images of post-washed scaffolds show increased porosity in the cross-section. Residual salt (bright white) is only visible in the 45% sample (FIG. 4B).

Example 3. Shaped PHB Scaffold

In this example, shaped scaffolds having non-spherical (FIG. 5A) and spherical (FIG. 5B) pores were prepared.

Figure 5:
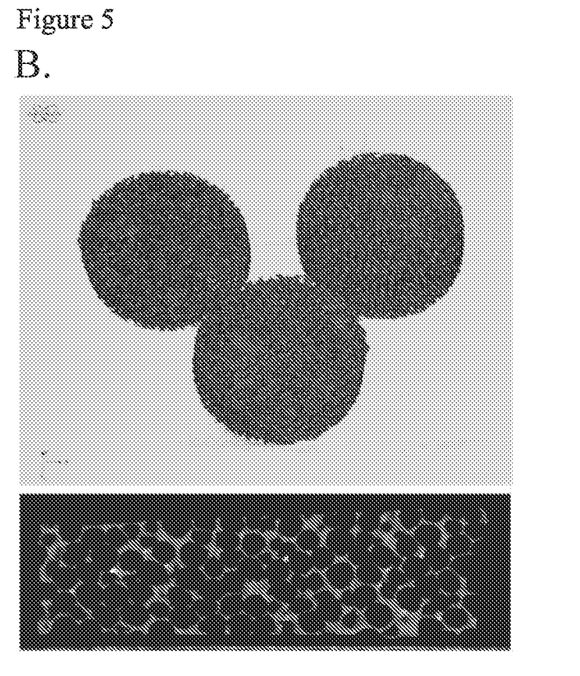
FIG. 5 is an illustration showing shaped scaffolds of the invention. The shaped scaffold shown in a) comprises non-spherical pores, and the shaped scaffold shown in b) comprises spherical pores.
Figure 5A:
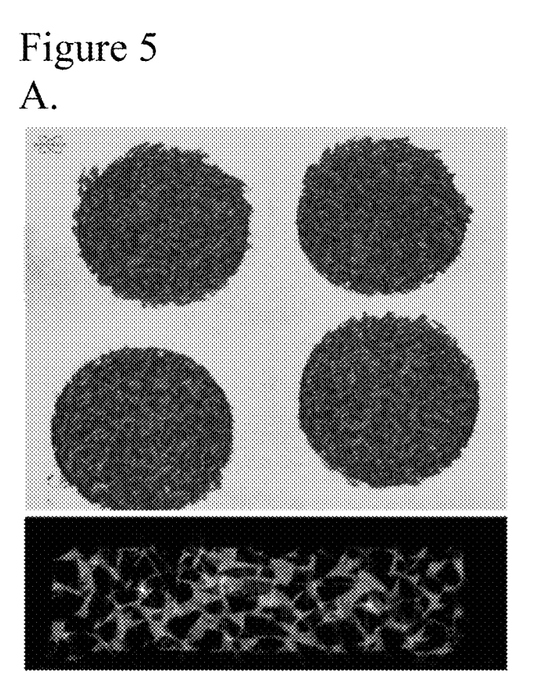

To prepare scaffolds with non-spherical pores, salt (425-600 μm) was mixed with PHB powder and compressed to 190° C. with 70 MPa pressure. Cores were drilled out of the compressed block and porogen was removed using water washes (FIG. 5A).

To prepare scaffolds with spherical pores, PMMA beads (425-500 μm) were mixed with PHB powder and compressed to 190° C. with 70 MPa pressure. Cores were drilled out of the compressed block and porogen was removed using acetone washes (FIG. 5B).

Example 4. Shaped PHB-PHV2% Scaffold

Figure 6:
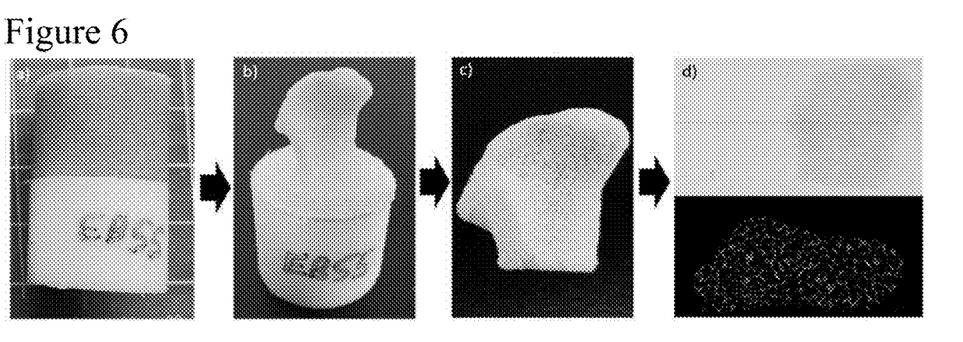
FIG. 6 is an illustration showing shaped scaffolds of the invention. As shown, a compressed block (a) is machined to an anatomical shape (b), followed by salt leaching step to create a porous scaffold having a desired shape (c). The porosity of the scaffold is shown in (d).

In this example, a bulk block of PHB-PHV2% polymer was prepared (FIG. 6A). The bulk was then machined with CNC to an anatomical shape (FIG. 6B), followed by a salt leaching step to create a porous scaffold having a desired shape (FIG. 6C). A microCT scan shows the porosity of the scaffold in FIG. 6D.

Example 5. Compression Pressure Experiment

In this example, PHB-PHV2% copolymer material was combined with 60% or 80% salt (450-600 μm) and heated to 185° C. as in Example 2. Compression forces were applied as set forth in Table 1 until the scaffolds could be both machined on lathe and leached without losing mechanical integrity.

TABLE 1

Compression Pressure Applied to PHB-PHV2% copolymer.

| Pressure (MPa) | 60% Porogen | 80% Porogen |
|---|---|---|
| 4.4 | Crumbled in lathe | Crumbled in lathe |
| 8.8 | Successfully lathed and washed | Fell apart during wash |
| 17.6 | — | Successfully lathed and washed |
| 105 | — | Successfully lathed and washed |

Figure 7:
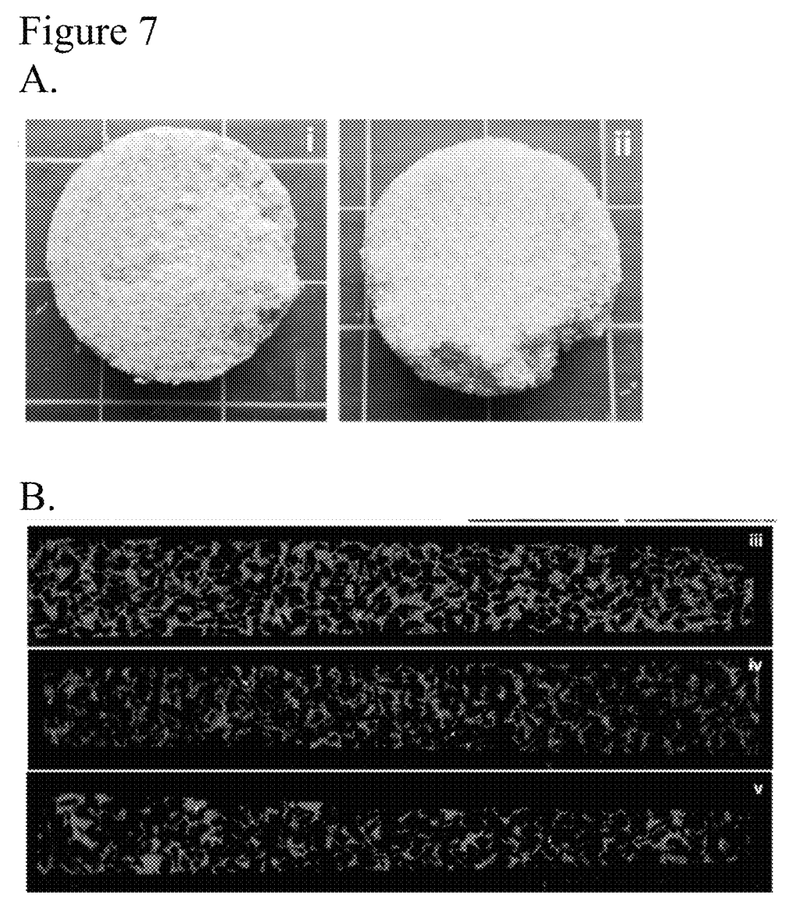
FIG. 7 is an illustration showing porous scaffolds of the invention that were prepared using various compression forces. The scaffolds shown in (a) contain (i) 60% and (ii) 80% salt and were prepared with 4.4 MPa pressure. As shown in the images, these scaffolds crumbled when shaped with a lathe. MicroCT images are shown in (b) of leached scaffolds prepared under increased pressure (iii) 60% salt at 8.8 MPa, (iv) 80% salt at 17.6 MPa and (v) 80% salt at 105 MPa.

When 4.4 MPa of pressure was applied, the scaffolds of both 60% and 80% porosity crumbled in the lathe. See FIG. 7A (60% porosity shown in (i) and 80% porosity shown in (ii)). When 8.8 Mpa pressure was applied, the 60% scaffold was successfully lathed and washed. However, μCT shows the presence of smaller voids, likely caused by small air pockets, not removed during compression process (FIG. 7B-iii). The 80% porogen scaffold fell apart during wash even though it was prepared under the same pressure as the 60% porogen scaffold. Thus, different composition scaffolds may have different minimum compression pressures. A 80% porogen scaffold was successfully produced with 17.6 Mpa (FIG. 7B iv) The highest pressure (105 MPa) scaffold showed the absence of the small voids, but a high interconnectivity between voids, likely caused by the increased pressure (FIG. 7B-v).

Example 6. Culture of Human Mesenchymal Stem Cells

Human mesenchymal stem cells were harvested from human adipose tissue and cultured in cell culture medium supplemented with osteogenic inducing factors. Medium was changed 2 times per week and cultured for 3 passages until confluence (14 days).

Example 7. PHB-PHV2% Scaffold Supports Cell Attachment and Growth

Figure 8:
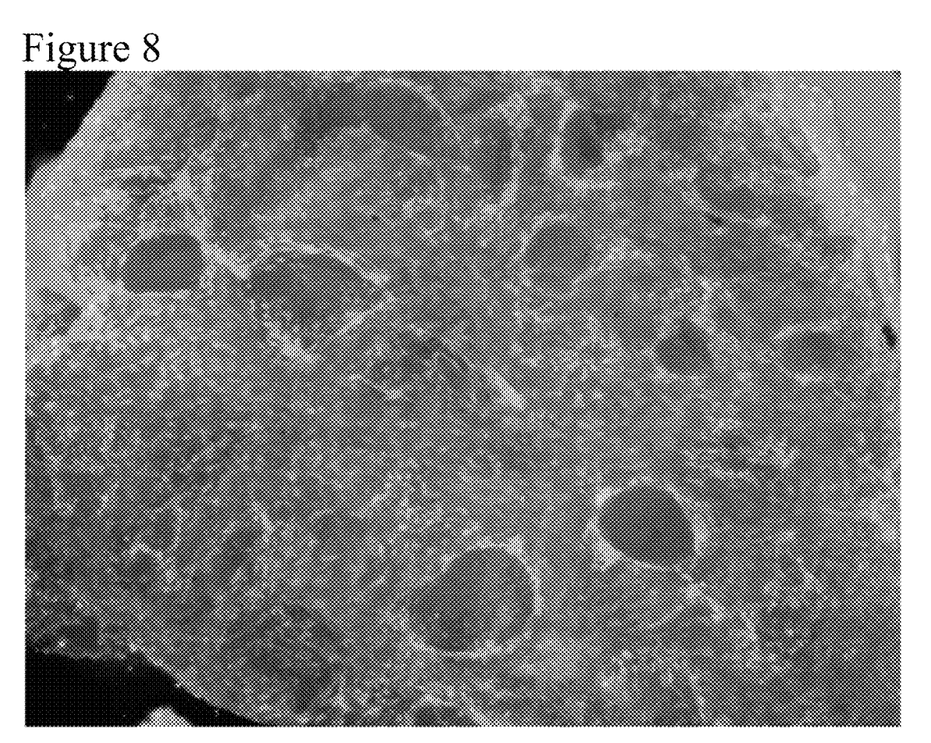
FIG. 8 is an image showing mesenchymal stem cells cultured on a porous PHB-PHV2% scaffold for 7 days. Live/dead imaging (4x) reveals a confluent covering of live cells on the scaffold material.

Adipose-derived human mesenchymal stem cells were cultured on porous PHB-PHV2% scaffolds for 7 days. Live/dead imaging (4x) reveals a confluent covering of live cells on this material (FIG. 8).

Example 8. Scaffold Seeding Experiment

Human adipose derived stem cells (hADSC) were seeded on PCL/hydroxyapatite scaffolds of the invention with a 75% porosity and cultured in osteogenic media. The methods for making these grafts, sterilizing them, and seeding with stem cells can be found in the attached appendix. Experimental data is also provided in the attached appendix.

Prophetic Example. Bone Regeneration Using Scaffold Implant

In this example, a porous polymer scaffold is provided. hADSCs cells adhere, divide and differentiate on the scaffold over the course of 3 weeks. At the end of three weeks the cellularized scaffold is tested as follows: 1) H+E histology to confirm cell attachment and proliferation, 2) DNA quantization to confirm the final amount of cells in the scaffold, 3) expression of osteogenic markers (genetic or protein) to confirm differentiation of the stem cells to the osteogenic lineage, and 4) mineral quantization to confirm the deposition of minerals by the differentiated hADSCs.

The scaffolds can be milled in to anatomically correct shapes. After cellularization, the scaffolds can be implanted using conventional methods to replace bone lost due to trauma, congenital defects or cancer.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of preparing a porous scaffold comprising a biodegradable polymer and a ceramic material, the porous scaffold having a desired shape and comprising interconnected pores and an average porosity of about 50% to about 90% by volume, the method comprising the steps of:
   heating a mixture comprising the biodegradable polymer, the ceramic material, and a porogen, wherein the biodegradable polymer is selected from the group consisting of polycaprolactone, polyhydroxybutyrate, and poly(3-hydroxybutyrate-co-3-hydroxyvalerate), and wherein the ceramic material is tricalcium phosphate;
   compressing the heated mixture at a pressure of about 35 MPa to about 110 MPa;
   cooling the compression to room temperature to form a bulk substrate;
   selectively removing a material from the bulk substrate to afford a shaped substrate; and
   removing the porogen from the shaped substrate to afford the porous scaffold having a desired shape,
   wherein the scaffold comprises at least about 50% by volume of ceramic material, and wherein the heating step involves heating the mixture to the melting temperature of the biodegradable polymer.

2. The method of claim 1, wherein the step of selectively removing material from the bulk substrate comprises excising at least some of the bulk substrate by way of milling, lathing, drilling or cutting the bulk substrate to afford a desired shape.

3. The method of claim 1, wherein the average porosity is in the range of about 60% to about 80% by volume.

4. The method of claim 1, wherein the pores of the scaffold have an average pore size of about 450 μm to about 600 μm.

5. The method of claim 1, wherein a variation in average pore size throughout the scaffold is less than about 10% by volume.

6. The method of claim 1, wherein the porogen comprises sodium chloride or poly(methyl methacrylate).

7. The method of claim 1, wherein the heating is carried out at temperature of about 185° C. to about 190° C.

8. The method of claim 1, wherein the compressing is carried out at a pressure of about 70 MPa.

9. The method of claim 1, wherein the desired shape is an anatomical shape.

10. The method of claim 1, wherein the desired shape is in the form of a biological tissue.

11. The method of claim 1, wherein the desired shape is in the form of a bone graft.

12. The method of claim 1, wherein the scaffold further comprises a bioactive agent.

13. The method of claim 12, wherein the bioactive agent is selected from the group consisting of: stem cells, bone marrow, plasma, growth factors, antibiotics, and immunosuppressive agents, or combinations thereof.

14. The method of claim 12, wherein the bioactive agent comprises stem cells.

15. The method of claim 12, wherein the scaffold is a suitable platform for stem cell differentiation.

16. The method of claim 15, wherein said stem cells are mesenchymal stem cells.

17. The method of claim 1, wherein the porous polymer scaffold has an average porosity of 80% to 90% by volume.

18. The method of claim 1, wherein the porous polymer scaffold has an average porosity of 90% by volume.

19. The method of claim 1, wherein the porous polymer scaffold comprises 50% by volume of tricalcium phosphate.

* * * * *